United States Patent [19]

Kalender

[11] Patent Number: 5,301,672
[45] Date of Patent: Apr. 12, 1994

[54] RADIOLOGICAL DIAGNOSTICS SYSTEM EMPLOYING A CONTRAST AGENT

[75] Inventor: Willi Kalender, Kleinseebach, Fed. Rep. of Germany

[73] Assignee: Siemens Aktiengesellschaft, Munich, Fed. Rep. of Germany

[21] Appl. No.: 977,053

[22] Filed: Nov. 16, 1992

[30] Foreign Application Priority Data

Dec. 9, 1991 [DE] Fed. Rep. of Germany ....... 4140552
Jun. 3, 1992 [DE] Fed. Rep. of Germany ....... 4218321

[51] Int. Cl.$^5$ .............................................. A61B 6/00
[52] U.S. Cl. ................... 128/654; 128/653.1; 128/653.4; 128/687; 378/97
[58] Field of Search .......... 128/654, 653.1, 653.4, 128/632, 633, 665, 687; 378/51, 62, 64, 97, 99; 250/336.1

[56] References Cited

U.S. PATENT DOCUMENTS

| | | | |
|---|---|---|---|
| 4,459,990 | 7/1984 | Barnea | 128/654 |
| 4,528,178 | 7/1985 | Babb | 128/653.1 |
| 5,005,576 | 4/1991 | Günther | 128/665 |
| 5,040,538 | 8/1991 | Mortazavi | 128/633 |
| 5,057,695 | 10/1991 | Hirao et al. | 128/633 |
| 5,067,494 | 11/1991 | Rienmueller et al. | 128/653.1 |
| 5,074,309 | 12/1991 | Gerdt | 128/687 |
| 5,128,121 | 7/1992 | Berg et al. | 128/653.4 |

*Primary Examiner*—Paul Prebilic
*Attorney, Agent, or Firm*—Hill, Steadman & Simpson

[57] ABSTRACT

In a diagnostics system wherein a radiological image is generated of a patient who has been injected with a contrast agent, the arrival of the contrast agent bolus at the imaging site is identified either directly by detecting the contrast agent, or indirectly by detecting a dye injected with the contrast agent, so that a synchronization of the imaging exposures with the arrival of the contrast agent can be assured. If a dye is used, the dye can be an optically detectable dye which is injected via the contrast agent syringe in addition to the contrast agent. A densitometer identifies the arrival of the contrast agent or of the dye at a predetermined location of the patient, and controls triggering of the exposures.

3 Claims, 1 Drawing Sheet

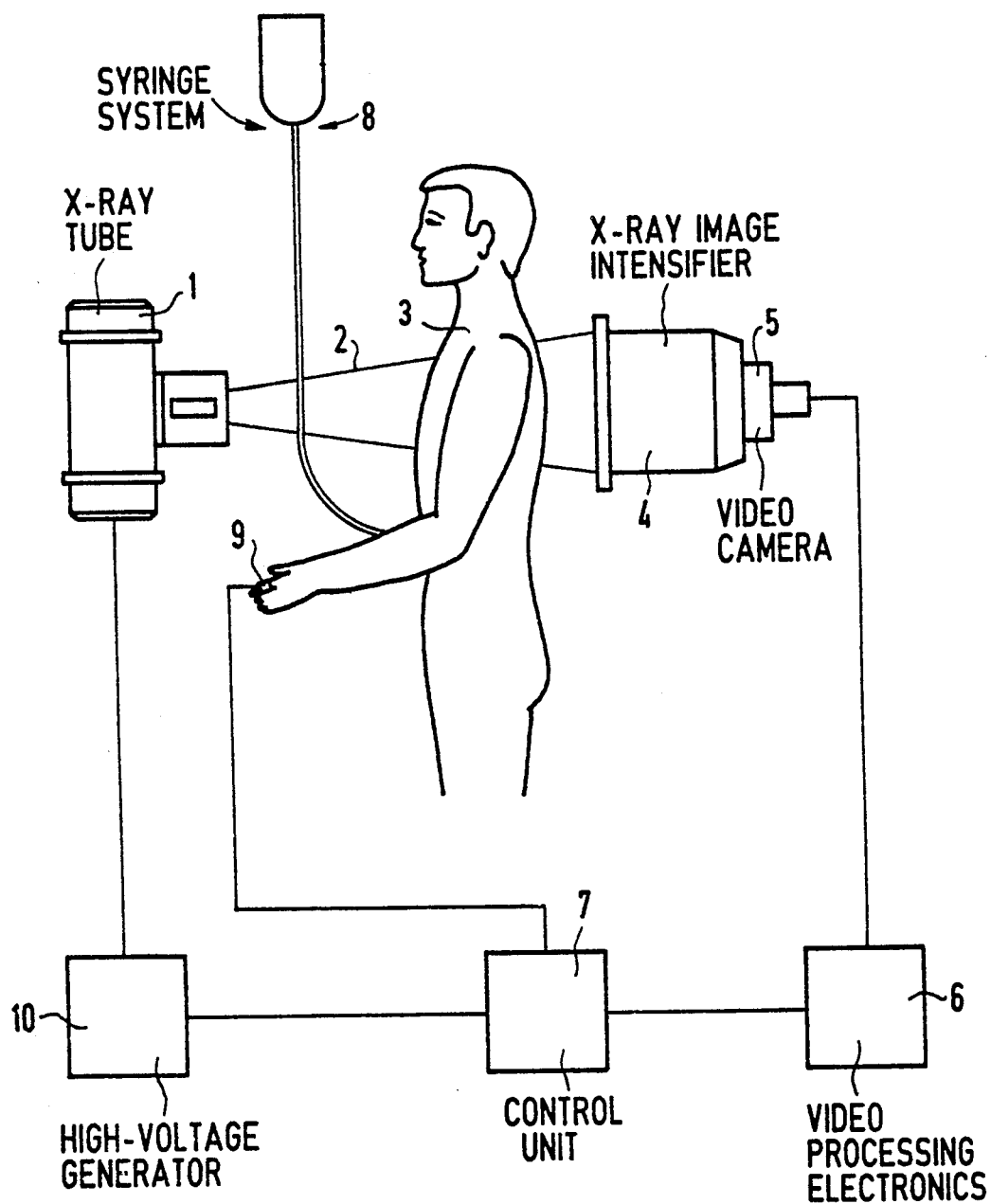

RADIOLOGICAL DIAGNOSTICS SYSTEM EMPLOYING A CONTRAST AGENT

BACKGROUND OF THE INVENTION

1. Field of the Invention

The present invention is directed to a radiological diagnostics system of the type wherein a radiological image of an examination subject, who has been injected with a contrast agent, is generated.

2. Description of the Prior Art

For many radiological investigations, it is desirable to trigger the imaging exposure, after the injection of a bolus of contrast agent, at exactly the time of arrival of the bolus of contrast agent in the organ or body region of interest, in order to achieve optimum contrast and/or to completely image the bolus if the examination is a dynamic examination. A problem in obtaining such exact triggering is that the passage time of the intravenously injected bolus (usually injected into the vein of an arm) through the right atrium, right ventricle, circulation through the lungs, the left atrium and left ventricle and to the organ of interest varies greatly from patient to patient. In addition to being dependent on parameters such as the heart rate, which can be relatively easily acquired, this passage time is dependent on other parameters which cannot be reliably monitored. A current problem is to obtain such synchronization in the context of spiral computer tomography, wherein complete organs or body sections are to be examined in the shortest possible time, and thus exact synchronization of the imaging with arrival of the contrast agent bolus is necessary. Frequently, a portrayal of blood vessels (CT angiography) is also desired. The triggering problem, however, is present in all examinations which require an injection of a contrast agent.

The above problem has not been exactly resolved, but has heretofore been approximately resolved by relying on the experience of the physician or radiologist. The examining person acquires the appropriate experience through examination employing transillumination monitoring, for example in digital subtraction angiography. Recommendations for estimating the passage time after injection of the contrast agent bolus, primarily dependent on the pulse rate, have been developed on the basis of such examinations and other fundamental studies. Such procedural rules, however, provide only approximate suggestions, resulting in the imaging exposure being triggered too early or too late in many instances, particularly in the case of examining personnel with less experience. If the x-ray imaging is triggered prematurely, this results in an unnecessary increase in the radiation dose to the patient. If the x-ray imaging is triggered too late, the image of the bolus is not completely acquired, which can mean that the results of the examination are not useable, and the entire examination must be repeated. The problem does not lend itself to a procedural protocol which is applicable in all examinations since, for example, the circulation parameters of a patient can change very rapidly.

SUMMARY OF THE INVENTION

It is an object of the present invention to provide a radiological diagnostics system of the type wherein the patient is injected with a contrast agent, wherein an exact synchronization of the imaging exposures with the course of the contrast agent is achieved, so that the exposures are made at a time when the contrast agent optimally fills the body region under examination.

The above object is achieved in accordance with the principles of the present invention in a diagnostics system wherein the circulation or diffusion of the contrast agent in the arterial system is monitored by a densitometer at a predetermined location of the patient, with the triggering of the exposures being controlled by the densitometer output. The contrast agent detection can ensue directly by measuring concentration of the contrast agent itself, for example on the basis of a low-energy and low-intensity radioisotope source. Alternatively, the contrast agent detection can be made indirectly by injecting an optically detectable dye as a contrast agent indicator into the patient through the contrast agent syringe in addition to the contrast agent. The course of the contrast agent can then be acquired by an optical densitometer. As used herein generically, however, the term "densitometer" means any type of instrument for identifying the in vivo concentration (density) of the contrast agent at a given location in the body.

The imaging exposures are then triggered at a time when the proper contrast agent occupation of the region under examination is present, by synchronizing the triggering of the exposures with the output signals of the densitometer. If necessary, a predetermined delay can be incorporated between the time at which the contrast agent concentration is measured at the selected body location and the actual triggering.

DESCRIPTION OF THE DRAWINGS

The single FIGURE is a schematic block diagram of a diagnostics system constructed in accordance with the principles of the present invention.

DESCRIPTION OF THE PREFERRED EMBODIMENTS

As shown in the drawing, a diagnostics installation constructed in accordance with the principles of the present invention includes an x-ray tube 1 which is operated by a high-voltage generator 10 so as to generate an x-ray beam 2 which transilluminates a patient 3. The radiation attenuated by the patient 3 is incident on the input screen of an x-ray image intensifier 4, having a video camera 5 which generates video signals corresponding to the x-ray (radiological) image for processing by video electronics 6. The video electronics 6 includes a television monitor (not separately shown) on which the image is visually displayed. The preparation of the x-ray exposures is controlled and synchronized by a control unit 7, connected both to the high-voltage generator 10 and to the video processing electronics 6. A syringe system 8 is provided for injecting a contrast agent into the patient 3. The contrast agent may be injected through the syringe system 8 in combination with a contrast agent indicator, such as an optically detectable dye. If a dye is used in combination with the contrast agent, this can be mixed with the contrast agent in a single drip bottle or drip packet, or separate drip bottles or packets can be used for the contrast agent and for the dye, combined by means of a Y-coupling in the syringe system 8, or by other suitable means.

the concentration of the contrast agent or the added dye (indicator) is acquired by a densitometer 9, which in the exemplary embodiment of FIG. 1 is shown arranged at a finger of the patient 3. It will be understood that the concentration of the contrast agent or dye can also be monitored at some other body location, for example, at an earlobe. The densitometer 9 supplies electrical output signals to the control unit 7, which function as trigger signals for the imaging. Imaging is triggered when the output signal from the densitometer 9 indicates a suitable occupation of the contrast agent 9 in the arterial system which indicates a simultaneous optimum occupation in the imaging region, or which indicates that an optimum presence of the contrast agent in the imaging region will occur following a predetermined delay.

An example of indirect detection employing the system shown in the drawing is as follows. Shortly before, or simultaneously with, the injection of the contrast agent bolus, an optically detectable dye is injected into the patient 3 through the syringe system 8. The arrival of this dye in the arterial system is detected by a change in the light transmission in a peripheral body part, such as the finger of the patient 3. The densitometer 9 continuously transmits output signals to the control unit 7. The control unit 7 forwards a trigger signal to the high-voltage generator 10 and to the video processing electronics 6 for triggering generation of an exposure when the dye is detected in a specified concentration and when the signal reaches a predetermined level. The video processing electronics 6 or the video camera 5 can have a delay incorporated therein, dependent on whether the dye was injected shortly before the contrast agent bolus or simultaneously therewith.

Although modifications and changes may be suggested by those skilled in the art, it is the intention of the inventor to embody within the patent warranted hereon all changes and modifications as reasonably and properly come within the scope of his contribution to the art.

I claim as my invention:

1. A diagnostics system comprising:
   means for generating a radiological image of a patient;
   means for introducing a contrast agent and a contrast agent indicator into said patient;
   means for identifying the in vivo concentration of said contrast agent in said patient at a predetermined location in the body of said patient by monitoring the presence of at least one of said contrast agent or said contrast agent indicator at said location, and for generating an electrical signal corresponding to said concentration; and
   means for triggering generation of said radiological image when said signal reaches a predetermined level.

2. A diagnostics system as claimed in claim 1 wherein said means for introducing a contrast agent and a contrast agent indicator is a syringe system.

3. A diagnostics system as claimed in claim 1 wherein said contrast agent indicator is an optically detectable dye, and wherein said means for identifying the in vivo concentration of said contrast agent is a means for optically monitoring the presence of said optically detectable dye at said location on the body of said patient.

* * * * *